US012718603B2

(12) United States Patent
Liu et al.

(10) Patent No.: US 12,718,603 B2

(45) Date of Patent: Aug. 25, 2026

(54) DEEP NEURAL NETWORK-BASED METHOD FOR DETECTING LIVING CELL MORPHOLOGY, AND RELATED PRODUCT

(71) Applicants: INSTITUTE OF AUTOMATION, CHINESE ACADEMY OF SCIENCES, Beijing (CN); UNIVERSITY OF CHINESE ACADEMY OF SCIENCES, Beijing (CN); SPERMCATCHER (BEIJING) BIOTECHNOLOGY CO., LTD, Beijing (CN)

(72) Inventors: Guole Liu, Beijing (CN); Jie Jin, Beijing (CN); Hao Shi, Beijing (CN); Yuqiang Jiang, Beijing (CN); Ge Yang, Beijing (CN); Tao Yang, Beijing (CN)

(73) Assignees: INSTITUTE OF AUTOMATION, CHINESE ACADEMY OF SCIENCES, Beijing (CN); UNIVERSITY OF CHINESE ACADEMY OF SCIENCES, Beijing (CN); SPERMCATCHER (BEIJING) BIOTECHNOLOGY CO., LTD, Beijing (CN)

( * ) Notice: Subject to any disclaimer, the term of this patent is extended or adjusted under 35 U.S.C. 154(b) by 445 days.

(21) Appl. No.: 18/276,350

(22) PCT Filed: Apr. 1, 2022

(86) PCT No.: PCT/CN2022/084777

§ 371 (c)(1), (2) Date: Aug. 8, 2023

(87) PCT Pub. No.: WO2022/167005

PCT Pub. Date: Aug. 11, 2022

(65) Prior Publication Data

US 2024/0119747 A1 Apr. 11, 2024

(30) Foreign Application Priority Data

Feb. 8, 2021 (CN) ........................ 202110169830.7

(51) Int. Cl.
*G06T 7/00* (2017.01)
*G06V 20/69* (2022.01)
(Continued)

(52) U.S. Cl.
CPC .......... *G06V 20/695* (2022.01); *G06T 7/0012* (2013.01); *G06V 20/698* (2022.01);
(Continued)

(58) Field of Classification Search
CPC .... G06V 20/695; G06V 20/698; G06V 10/82; G06V 2201/03; G06V 10/26;
(Continued)

(56) References Cited

U.S. PATENT DOCUMENTS

2018/0322327 A1 11/2018 Smith et al.
2018/0322660 A1 11/2018 Smith
(Continued)

FOREIGN PATENT DOCUMENTS

CN 102647561 A 8/2012
CN 108913599 A 11/2018
(Continued)

OTHER PUBLICATIONS

European Search Report for EP22749284.0 issued on Jan. 14, 2025 from European patent office in a counterpart European patent application ( See the highlight sentences of Part 1, p. 1-4; the highlight sentences of Part 2, p. 4).
(Continued)

*Primary Examiner* — Han Hoang

(74) *Attorney, Agent, or Firm* — The PL Law Group, PLLC

(57) ABSTRACT

A deep neural network-based method for detecting living cell morphology may include identifying and locating one or
(Continued)

more living cells within an acquired image to be detected by using a deep neural network-based target detection model, so as to extract one or more living single cell images. segmenting the image of the one or more living single cells by using a deep neural network-based cell segmentation model, so as to obtain one or more feature part of the one or more living single cells. and analyzing and determining a morphological parameter of the one or more living single cells based on the one or more feature parts. Thus, the activity of the detected cells can be ensured, and a non-destructive, accurate, and rapid detection of living cell morphology can be achieved.

17 Claims, 7 Drawing Sheets

(51) Int. Cl.
*G16B 20/00* (2019.01)
*G06V 10/82* (2022.01)

(52) U.S. Cl.
CPC .... *G16B 20/00* (2019.02); *G06T 2207/20036* (2013.01); *G06T 2207/20081* (2013.01); *G06T 2207/20084* (2013.01); *G06T 2207/30024* (2013.01); *G06T 2207/30168* (2013.01); *G06V 10/82* (2022.01); *G06V 2201/03* (2022.01)

(58) Field of Classification Search
CPC .. G06V 10/774; G06V 10/764; G06T 7/0012; G06T 2207/20036; G06T 2207/20081; G06T 2207/20084; G06T 2207/30024; G06T 2207/30168; G06T 7/10; G06T 2207/10056; G06T 2207/30004; G16B 20/00; G06N 3/048; G06N 3/0464; G06N 3/09; G06N 3/045; G06N 3/08
See application file for complete search history.

(56) References Cited

U.S. PATENT DOCUMENTS

| | | | | |
|---|---|---|---|---|
| 2019/0114774 | A1* | 4/2019 | Zhang | G06N 3/08 |
| 2020/0388033 | A1* | 12/2020 | Matlock | G06V 10/774 |
| 2021/0374952 | A1* | 12/2021 | Shafiee | G06T 5/30 |
| 2022/0392062 | A1* | 12/2022 | Chavez Badiola | G06V 10/26 |
| 2024/0212370 | A1* | 6/2024 | Nakamura | C12Q 1/02 |

FOREIGN PATENT DOCUMENTS

| | | | |
|---|---|---|---|
| CN | 110458821 | A | 11/2019 |
| CN | 110705639 | A | 1/2020 |
| CN | 111563550 | A | 8/2020 |
| CN | 112036384 | A | 12/2020 |
| CN | 112135048 | A | 12/2020 |
| CN | 112330660 | A | 2/2021 |
| CN | 112508955 | A | 3/2021 |
| WO | WO 2020/068380 | A1 | 4/2020 |

OTHER PUBLICATIONS

International Search Report for PCT/CN2022/084777 mailed on Jun. 8, 2022.

Office action issued on Mar. 25, 2021 from China Patent Office in a counterpart China Patent Application No. 202110169830.7 (all the cited references are listed in this IDS.) (English translation is also submitted herewith.).

Office action issued on Apr. 19, 2021 from China Patent Office in a counterpart China Patent Application No. 202110169830.7 (all the cited references are listed in this IDS.) (English translation is also submitted herewith.).

Office action issued on May 18, 2021 from China Patent Office in a counterpart China Patent Application No. 202110169830.7 (all the cited references are listed in this IDS.) (English translation is also submitted herewith.).

Wang. Yongxin, "Research on Sperm Morphology Evaluation and Morphological Classification", Medicine and Health Sciences, Chinese Master's Theses Full-Text Database, Jun. 15, 2014, Huazhong University of Science & Technology (English Abstract is included in the fifth and sixth pages.).

Ya Ping. Liu et al., "Follicle-stimulating hormone may predict sperm retrieval rate and guide surgical approach in patients with non-obstructive azoospermia", Reproductive Biology, Nov. 4, 2020, vol. 20(4), pp. 573-579 (English translation of Abstract is submitted herewith.).

Malte S. Nissen et al., "Convolutional neural networks for segmentation and object detection of human semen", Scandinavian Conference on Image Analysis, Apr. 3, 2017, http://arXiv:1704.00498v1.

Wang Cbuanzhong et al., "Sharpness Measurement for Microscopic Cell Image of Variable Content", Journal of Test and Measurement Technoligy, 2012, vol. 26(2), pp. 93-97, DOI:10.3969/j.issn.1671-7449.2012 02.001 (English Abstract is included in the first page.).

* cited by examiner

DEEP NEURAL NETWORK-BASED METHOD FOR DETECTING LIVING CELL MORPHOLOGY, AND RELATED PRODUCT

PRIORITY

This application claims benefit under 35 U.S.C. 119, 120, 121, or 365(c), and is a National Stage entry from International Application No. PCT/CN2022/084777 filed on Apr. 1, 2022, which claims priority to the benefit of Chinese Patent Application No. 202110169830.7 filed in the Chinese Intellectual Property Office on Feb. 8, 2021, the entire contents of which are incorporated herein by reference.

BACKGROUND

1. Technical Field

The present disclosure generally relates to the field of neural network technology. More specifically, the present disclosure relates to a deep neural network-based method for detecting living cell morphology, and related products.

2. Background Art

Cell morphology detection is significant for assessing cell status and cell quality. However, relevant methods for cell morphology detection are mostly based on recognition of images of fixed and stained cells, without the capability of online detection of living cells, especially actively moving living cells.

Taking sperm cells as an example, the conventional methods for sperm morphology detection involve preprocessing semen specimens through centrifugation, smearing, staining, etc., followed by manual observation of the sperm smear under a microscope, and classification of sperm morphology based on the examiner's experience or using computer-aided classification technology for image classification of the sperm smear. However, the fixed staining process and methods may have some effect on the morphology structure of the sperm, which might influence the accuracy of morphology detection results. Moreover, performing smearing, staining, and other preprocessing on sperm cells will destroy their physiological functions and DNA, causing sperm inactivation, making the tested sperm unusable for clinical purposes, thereby limiting the applicability of the above methods. For instance, in vitro fertilization technology requires living sperm cells, and due to the lack of methods for detecting living cell morphology, the selection of living sperm for in vitro fertilization still relies on manual operations by clinical staff. This reliance heavily depends on the experience of the clinical staff, leading to a detection process that is highly subjective, non-uniform in standards, and inefficient. Therefore, how to realize non-destructive, rapid, and accurate detection of living cell morphology is a technical problem that urgently needs to be solved.

SUMMARY

In view of the technical problems mentioned above, the technical solutions of the present disclosure provide a method, an apparatus, a device, a system, and a computer storage medium for detecting living cell morphology based on deep neural networks in multiple aspects.

In a first aspect of the present disclosure, a deep neural network-based method is provided for detecting living cell morphology, including: identifying and locating one or more living cells within an acquired image to be detected by using a deep neural network-based target detection model, so as to extract one or more living single cell images; segmenting the living single cell image by using a deep neural network-based cell segmentation model, so as to obtain one or more feature parts of the living single cell(s); and analyzing and determining a morphological parameter of the living single cell(s) based on the feature part(s).

According to an embodiment of the present disclosure, prior to using the target detection model to identify and locate one or more living cells within an acquired image to be detected, the method may further include: obtaining a large number of samples of living cell images; performing a first annotation on individual cells in the living cell images; and training a first deep neural network model using the first annotated living cell images to obtain the target detection model.

According to another embodiment of the present disclosure, prior to using the cell segmentation model to segment the living single cell image(s), the method may further include: performing a second annotation on feature parts of individual cells in acquired living cell images; and training a second deep neural network model using the second annotated living cell images to obtain the cell segmentation model.

According to yet another embodiment of the present disclosure, during training of the first deep neural network model, the method may include applying image data enhancement processing to the living cell images, where the image data enhancement processing includes at least one of spatial transformation processing, scale resizing processing, and image brightness adjustment processing.

According to an embodiment of the present disclosure, during training of the second deep neural network model, the method may include applying image data enhancement processing to the living cell images, where the image data enhancement processing includes at least one of spatial transformation processing, scale resizing processing, and image brightness adjustment processing.

According to another embodiment of the present disclosure, an output part of the cell segmentation model adopts a single-branch multi-class segmentation structure or a multi-branch single-class segmentation structure.

According to yet another embodiment of the present disclosure, the living cell includes a living sperm, and the feature part includes at least one of a sperm head, a vacuole, a midpiece, and a tail.

According to an embodiment of the present disclosure, before segmenting the living single cell image(s) by using the cell segmentation model, the method may further include: classifying living single cell images through focal plane imaging to select a single cell image located within the focal plane range; and the segmenting the living single cell image may include segmenting the single cell image located within the focal plane range.

According to another embodiment of the present disclosure, the classifying living single cell images through focal plane imaging to select a single cell image located within the focal plane range may include: classifying images of cell samples collected at different focal planes and taking them as focal plane image sample datasets; using the focal plane image sample datasets to train a third deep neural network model to obtain a focal plane classification model; and using the focal plane classification model to classify living single cell images through focal plane imaging to select a single cell image within the focal plane range.

According to yet another embodiment of the present disclosure, during training the third deep neural network model, the method may include applying image data enhancement processing to the focal plane image sample datasets, where the image data enhancement processing includes at least one of spatial transformation processing, scale resizing processing, and image brightness adjustment processing.

According to an embodiment of the present disclosure, the method may further include: before using the target detection model, the cell segmentation model, or the focal plane classification model, accelerating at least one of the target detection model, the cell segmentation model, or the focal plane classification model through network structure acceleration, model inference acceleration, and/or model pruning acceleration.

According to another embodiment of the present disclosure, the analyzing and determining the morphological parameter of the living single cells may include: performing morphological analysis on the segmented feature parts of the living single cells to obtain a geometric parameter of the feature parts; measuring sharpness of the living single cell images to further select a clear single cell image; and determining the morphological parameter of the living single cells based on the geometric parameter and the sharpness.

According to yet another embodiment of the present disclosure, measuring the sharpness of the living single cell images may include: evaluating the sharpness of the living single cell images with one or more focusing evaluation operators.

According to an embodiment of the present disclosure, determining the morphological parameter of the living single cells based on the geometric parameter and the sharpness may include: performing a first ranking of the living single cell images based on values of the geometric parameter; performing a second ranking of the living single cell images based on values of the sharpness; and based on the ranking, selecting one or more images that are in the forefront in both the first ranking and the second ranking, and using an average value of the geometric parameters of the selected one or more images as the morphological parameter of the living single cells.

According to another embodiment of the present disclosure, the geometric parameter includes at least one of length, width, area, ellipticity, quantity, and position.

According to an embodiment of the present disclosure, the image to be detected may include at least one of a differential interference contrast image, a phase contrast image, a bright field image, and a dark field image.

In a second aspect of the present disclosure, a device is provided for living cell morphology detection based on deep neural networks, including: a positioning module configured to identify and locate one or more living cells contained in an acquired image to be detected by using a deep neural network-based target detection model, so as to extract one or more living single cell image; a segmentation module configured to segment the living single cell image(s) by using a deep neural network-based cell segmentation model, so as to obtain one or more feature parts of the living single cell(s); and a morphology analysis module configured to analyze and determine a morphological parameter of the living single cell(s) based on the feature part(s).

According to one embodiment of the present disclosure, the device may further include: a focal plane classification module configured to perform focal plane imaging-based classification on the living single cell images, to select a single cell image located within the focal plane range; and the segmentation module may be further configured to segment the single cell image located within the focal plane range.

In a third aspect of the present disclosure, an apparatus is provided for living cell morphology detection based on deep neural networks, including: at least one processor; a memory storing program instructions that, when executed by the at least one processor, enable the apparatus to perform the method according to any one of the items described in the first aspect of the present disclosure.

In a fourth aspect of the present disclosure, there is provided a computer-readable storage medium storing a program for living cell morphology detection, which when run by a processor, carries out the method according to any one of the items described in the first aspect of the present disclosure.

In a fifth aspect of the present disclosure, a system is provided for living cell morphology detection based on deep neural networks, including: an image capturing unit for capturing an image containing a living cell to be detected; a control terminal communicatively connected to the image capturing unit and used to receive the image to be detected sent from the image capturing unit; and the apparatus as described in the third aspect of the present disclosure, communicatively connected to the control terminal, for receiving the image to be detected sent from the control terminal for detection, and sending detection results to the control terminal.

According to one embodiment of the present disclosure, the apparatus includes an inference machine.

Through the above description of the technical solution of the present disclosure and multiple embodiments thereof, those skilled in the art can understand that the deep neural network-based method for living cell morphology detection according to the present disclosure can determine a morphological parameter of a living single cell by using a target detection model to locate and extract the living single cell from an image to be detected, using a cell segmentation model to segment the living single cell, and analyzing based on feature part(s) obtained through the segmentation. According to the method of the present disclosure, the activity of the cell being detected can be ensured, and a non-destructive, accurate, and rapid detection of the living cell morphology is achieved, which is beneficial for the clinical application and research of the detected cell, and has significant meaning and application value.

BRIEF DESCRIPTION OF THE DRAWINGS

By reading the following detailed descriptions with reference to drawings, the above and other objects, features and technical effects of exemplary embodiments of the present disclosure will become easier to understand. In the drawings, several embodiments of the present disclosure are shown in an exemplary but not a restrictive manner, and the same or corresponding reference numerals indicate the same or corresponding parts.

DETAILED DESCRIPTION

Figure 1:
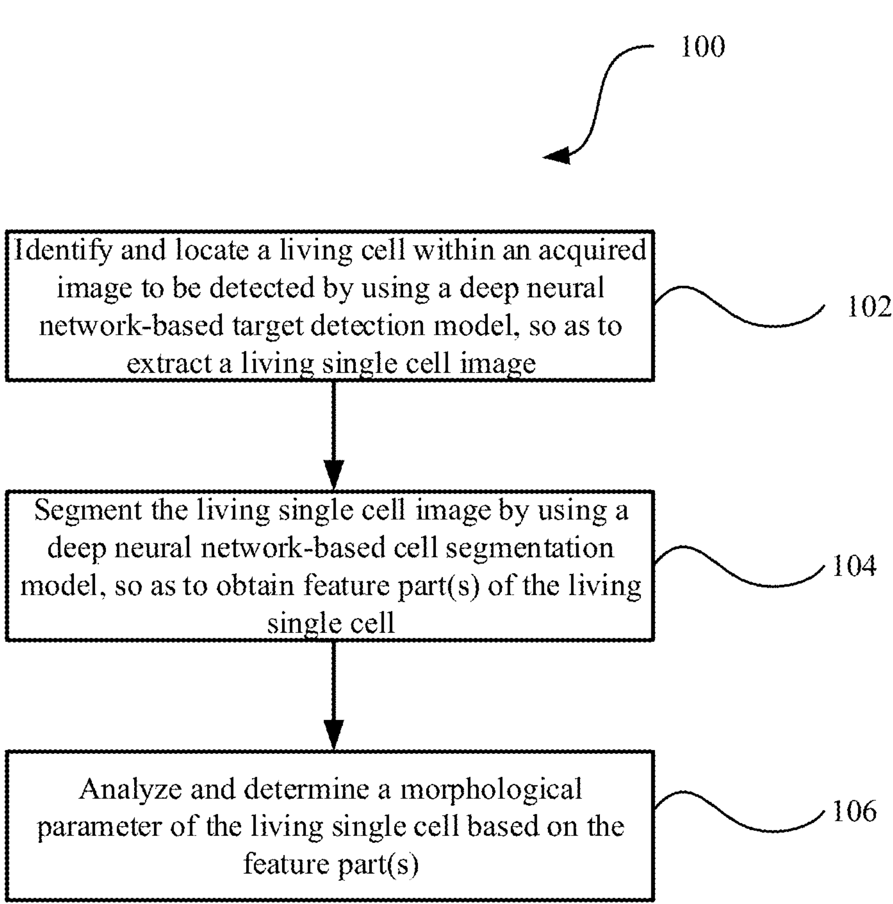
FIG. 1 is a flowchart generally showing a deep neural network-based method for living cell morphology detection according to an embodiment of the present disclosure.

Technical solutions in embodiments of the present disclosure will be described clearly and completely hereinafter with reference to the drawings in the embodiments of the present disclosure. Obviously, the embodiments to be described are merely some of, but not all of embodiments of the present disclosure. All other embodiments obtained by those of ordinary skill in the art based on the embodiments of the present disclosure without creative efforts shall fall within the protection scope of the present disclosure.

It should be understood that terms such as "first", "second", "third" and "fourth" that may be present in the claims, the specification, and the drawings are used for distinguishing different objects rather than describing a specific order. It should be understood that the terms "including" and "comprising" used in the specification and the claims indicate the presence of a feature, an entity, a step, an operation, an element, and/or a component, but do not exclude the existence or addition of one or more other features, entities, steps, operations, elements, components, and/or collections thereof.

It should also be understood that the terms used in the specification of the present disclosure are merely for the purpose of describing particular embodiment rather than limiting the present disclosure. As being used in the specification and the claims of the disclosure, unless the context clearly indicates otherwise, the singular forms "a", "an" and "the" are intended to include the plural forms. It should also be understood that the term "and/or" used in the specification and the claims refers to any and all possible combinations of one or more of relevant listed items and includes these combinations.

As used in this specification and claims, the term "if" can be interpreted as "when," "once," "in response to determining," or "in response to detecting," depending on the context. Similarly, the phrases "if determined" or "if detected [described condition or event]" can be interpreted to mean "once determined" or "in response to determining" or "once detected [described condition or event]" or "in response to detecting [described condition or event]."

There are many technical difficulties in implementation of living cell morphology detection, for example, living cells are not static targets, and their positioning is challenging; cells often go out of focus when active, and defocused images are unusable for morphology detection because of blurriness; and living cell images have much lower contrast than stained images, thus increasing the difficulty of cell morphology parameter detection. To address one or more shortcomings of relevant technology, the present disclosure provides a novel, feasible solution. Specifically, a deep neural network-based method of living cell morphology detection according to embodiments of the present disclosure can identify, locate, and segment feature part(s) of a living cell contained in images being detected, thereby achieving non-destructive detection of living cell morphology while ensuring their viability. As will be understood by those skilled in the art through the following description, the invention also provides ways to further improve detection accuracy and efficiency in multiple embodiments, such as classifying focal plane imaging of living single cell images before segmentation, and/or accelerating at least one model among target detection models, cell segmentation models, or focal plane classification models to further improve detection speed and efficiency. The specific embodiments of the present disclosure will be described in detail with reference to the accompanying drawings.

FIG. 1 is a flowchart generally showing a deep neural network-based method for living cell morphology detection according to an embodiment of the present disclosure. As shown in FIG. 1, at step 102 of the method 100, one or more living cell within an acquired image to be detected may be identified and located by using a deep neural network-based target detection model, so as to extract one or more living single cell image. In one embodiment, the deep neural network-based target detection model may adopt at least one model such as Yolo, Faster R-CNN, etc. The image to be detected can be captured through devices such as microscopes, cameras, etc. In one embodiment, the image to be detected may include at least one of a differential interference contrast image, a phase contrast image, a bright field image, and a dark field image. The image to be detected may contain images of one or more living cells. According to another embodiment of the present disclosure, the living cell may include a living sperm cell, a cancer cell, etc. Identifying and locating a living cell within the image to be detected may include identifying and locating each target living cell within the image to be detected to extract each living single cell image, and excluding the influence of impurities and other factors. For example, in one embodiment, with target living cells being living sperm cells, the method 100 may identify, locate and extract living sperm cell(s) within the image to be detected, to exclude the influence of other types of cells or impurities. In another embodiment, the method 100 may extract a living single cell image containing deformity such as a multi-headed living single cell.

According to one embodiment of the present disclosure, in the method 100, one living single cell image might be extracted from the image to be detected. According to another embodiment of the present disclosure, in the method 100, multiple living single cell images might be extracted from the image to be detected and can be separately detected and analyzed in subsequent steps. In one embodiment, when the image to be detected contains multiple living cells, the method 100 can number the multiple living cells, thereby enabling tracking of living cells in different frames of the images to be detected.

In the method 100, the identification and location of a living single cell within the image to be detected may be performed by identifying an entire living single cell or by identifying one or more specific feature parts of the living single cell. For ease of understanding, the following will take a living sperm as an example and combine FIGS. 2A to 3C for explanation.

Figures 2A, 2B, 2C, 3A, 3B, 3C:
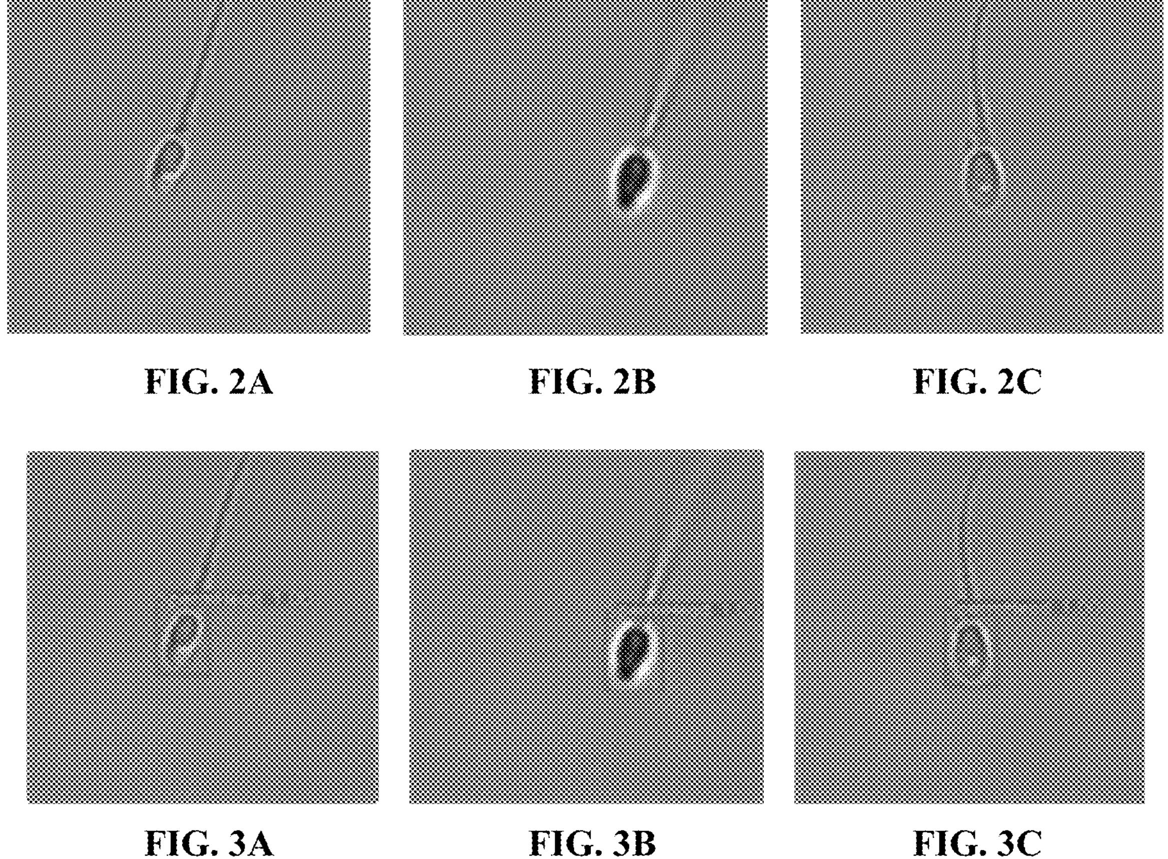
FIGS. 2A to 2C are schematic diagrams showing bright field images of a same living sperm in different postures according to an embodiment of the present disclosure.
FIGS. 3A to 3C are schematic diagrams showing localization results of the living sperm as shown in FIGS. 2A to 2C.

FIGS. 2A to 2C are schematic diagrams showing bright field images of a same living sperm in different postures according to an embodiment of the present disclosure. As shown by FIGS. 2A to 2C, due to the mobility and flipping of a living sperm, different images of a same living sperm in different postures are often captured when collecting images to be detected, making identification and localization more challenging. According to the method of the present disclosure, the living sperms in different postures within the living sperm images shown in FIGS. 2A to 2C can be identified and located, resulting in the location results shown in FIGS. 3A to 3C.

FIGS. 3A to 3C illustrate respectively the location results for the images FIGS. 2A to 2C. According to this embodiment, in the method 100, a living sperm can be identified and located by identifying a specific feature part (e.g., the head as shown) of the living sperm. As shown in FIGS. 3A to 3C, in one embodiment, the method 100 may display the location results with annotation boxes. According to the method of the present disclosure for identifying and locating a living cell within an image to be detected, living cells in different postures can be identified and located, which significantly improves the accuracy and reliability of the location.

Hereinafter, returning to FIG. 1, as shown in FIG. 1, at step 104, the method 100 may include segmenting the living single cell image(s) by using a deep neural network-based cell segmentation model, so as to obtain one or more feature parts of the living single cell(s). In one embodiment, the deep neural network-based cell segmentation model may include at least one of models such as U-net, FCN, DeepLab, E-net, etc. The segmentation results of the living single cell image(s) by the method 100 may vary depending on the type of the living single cell, i.e., the feature part to be segmented can be determined according to the type of the living single cell. The feature part of a living single cell may include one or more feature parts. For example, in one embodiment, the living cell may include a living sperm, and the feature part thereof may include at least one of a head, a vacuole, a midpiece, and a tail of the sperm.

According to another embodiment of the present disclosure, before using the target detection model or the cell segmentation model, in the method 100, at least one model of the target detection model and the cell segmentation model can be accelerated by using techniques such as network structure acceleration, model inference acceleration, and/or model pruning acceleration.

The network structure acceleration mentioned above can be achieved by using a simpler deep neural network, such as a lightweight neural network suitable for mobile terminals, such as MobileNet, ShuffleNet, etc. Compared with an ordinary convolutional neural network, MobileNet reduces the number of model parameters by using depth-wise separable convolutions. Model inference acceleration can be achieved by optimizing and reconstructing the network structure, reducing parameter precision, etc. Optimization and reconstruction of the network structure can include eliminating unnecessary output layers in the network to reduce computation, vertical integration of the network structure (e.g., the convolution layer 'cony', batch normalization 'BN', and rectified linear unit 'Relu' of the backbone neural network can be fused into a constant bit rate 'CBR' structure), horizontal integration of the network structure (e.g., merging layers with a same structure but different weights into a wider layer), etc. Reducing parameter precision can mean accelerating model inference by converting floating-point Float32 to half-precision Float16 or integer INT8 during model inference. Lower data precision will result in lower memory usage and latency, making the model smaller. Model pruning acceleration can be achieved during model inference by obtaining the output of each layer and neuron, and since units with zero or near-zero output has no or less contribution during inference, they can be cut off to reduce the computational cost of inference, thereby achieving the purpose of accelerating the model.

Then, the process moves to step 106 of the method 100, where a morphological parameter of the living single cell(s) can be analyzed and determined based on the feature part(s). The method 100 may determine the morphological parameter of the living single cell(s) by analyzing the morphology of the feature part(s). For example, according to an embodiment of the present disclosure, in the method 100, analyzing and determining the morphological parameter of the living single cell(s) may include: performing morphological analysis on the segmented feature part(s) of the living single cell(s) to obtain a geometric parameter of the feature part(s); measuring sharpness of the living single cell images to further select a clear single cell image; and determining the morphological parameter of the living single cell(s) based on the geometric parameter and the sharpness.

The above, in conjunction with FIG. 1, provides an illustrative description of a deep neural network-based method for detecting living cell morphology according to the present disclosure, which those skilled in the art can understand is exemplary and not limiting, and can be adjusted as needed. For example, the feature part of a living single cell can be adjusted and set according to the type of the living single cell. Also, for example, in another embodiment, the method 100 can further improve accuracy and efficiency of the living cell morphology detection by optimizing the target detection model or cell segmentation model, and screening the living single cell images, etc. The following will describe an exemplary embodiment of a deep neural network-based method for detecting living cell morphology according to the present disclosure in conjunction with FIG. 4.

Figure 4:
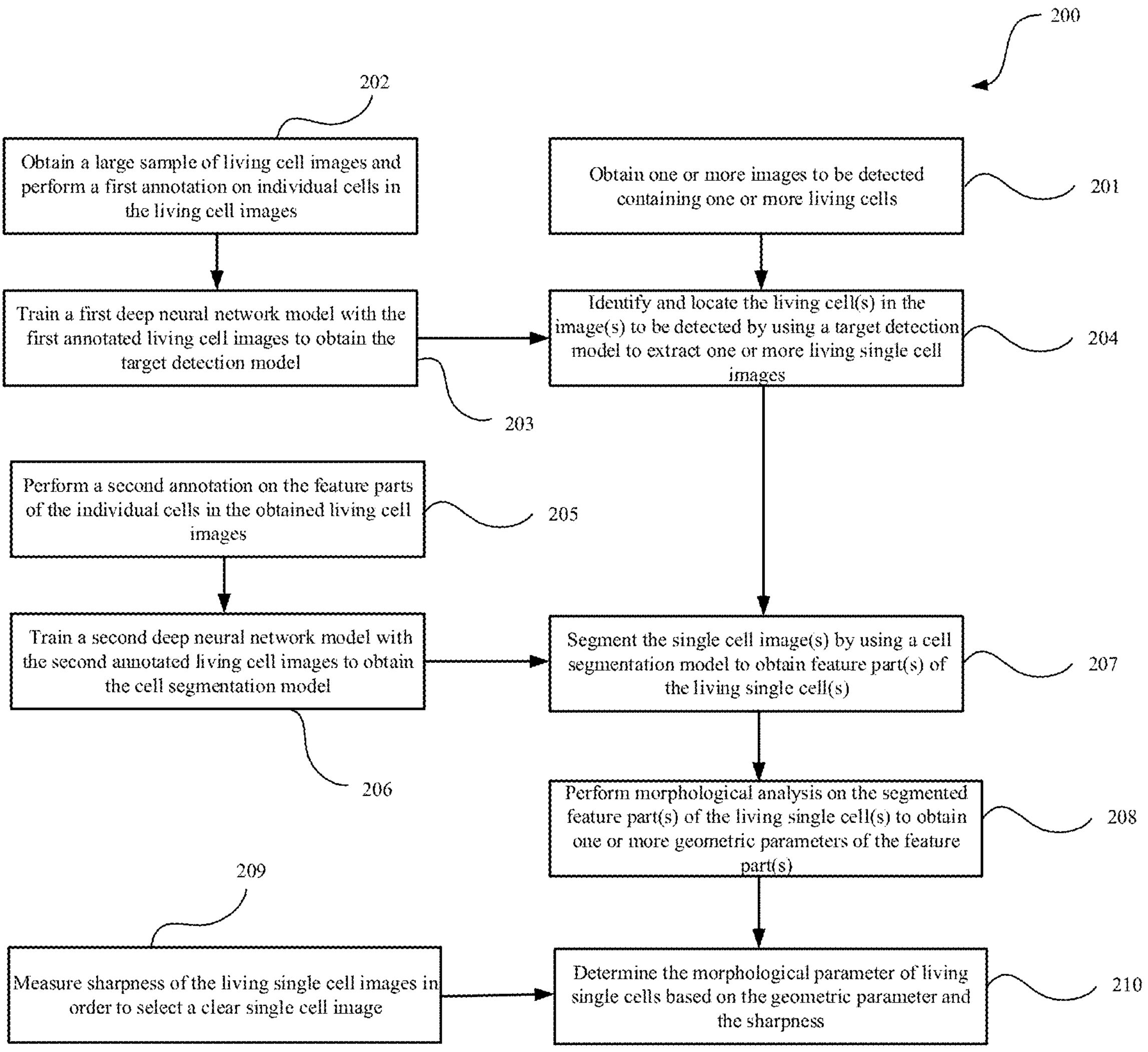
FIG. 4 shows a detailed flowchart of a deep neural network-based method for living cell morphology detection according to an embodiment of the present disclosure.

FIG. 4 shows a detailed flowchart of a deep neural network-based method 200 for living cell morphology detection according to an embodiment of the present disclosure. Through the following description, those skilled in the art will understand that the method 200 is a specific implementation of the method 100 shown in FIG. 1, so the previous description of the method 100 in FIG. 1 also applies to the method 200.

As shown in FIG. 4, at step 201 of the method 200, one or more images to be detected containing one or more living cells can be obtained directly or indirectly from, for example, a microscope or a camera, etc. Then, at step 204 of the method 200, a deep neural network-based target detection model can be used to identify and locate the living cell(s) in the images to be detected to extract one or more living single cell images. To further improve the accuracy of identification and location, one embodiment of the present disclosure further provides a preferred construction method for the target detection model, such as further shown in FIG. 4, before step 204, the method 200 may further include steps 202 and 203, which will be detailed below.

At step 202 of the method 200, a large sample of living cell images can be obtained, and a first annotation can be performed on individual cells in the living cell images. A large sample of living cell images can include a certain number of living cell images, the larger the quantity, the more conducive to improving the detection accuracy of the target detection model. In one embodiment, performing a first annotation on individual cells in the living cell images in the method 200 can include annotating a feature part of a single cell. In another embodiment, the first annotation on individual cells in the living cell images in the method 200 can be achieved by ways such as manual annotation or machine annotation. In yet another embodiment, in the method 200, the first annotation on individual cells in the living cell images can be achieved by using an annotation model.

Next, at step 203 of the method 200, the first annotated living cell images can be used to train a first deep neural network model to obtain the target detection model. In one embodiment, the first deep neural network model can be constructed based on at least one model such as Yolo, Faster R-CNN, etc. By using the first annotated living cell images to train the first deep neural network model, the parameters and weights of the first deep neural network model can be continuously optimized. In the method 200, the first annotated living cell images are used to train the first deep neural network model to obtain the trained first deep neural network model, which can be referred to as the target detection model.

According to another embodiment of the present disclosure, at step 203, during training of the first deep neural network model, the method 200 can further include applying image data enhancement processing to the living cell images, where the image data enhancement processing can include at least one of spatial transformation processing, scaling resizing processing, and image brightness adjustment processing, etc. Spatial transformation processing can include image processing methods such as scaling, rotation, perspective transformation, etc. Scaling resizing processing can include image processing methods such as proportional scaling or non-proportional scaling, etc. Image brightness adjustment processing can include image processing methods that brighten or darken the image as a whole or locally.

It should be noted that in the method 200, step 202 or 203 and step 201 can be executed simultaneously or in any order. In another embodiment, when the method 200 executes step 204, it can also simultaneously execute steps 202 and 203, continuously optimizing the parameters of the target detection model, so as to continuously adjust and improve the accuracy of identification and location.

Further, after step 204, the method 200 can proceed to step 207. At step 207, the method 200 can include using a deep neural network-based cell segmentation model to segment the living single cell image(s) to obtain one or more feature parts. To further improve the accuracy of feature part segmentation, an embodiment of the present disclosure further provides a preferred construction method for the cell segmentation model, such as further shown in FIG. 4, before step 207, the method 200 may further include steps 205 and 206, which will be detailed below.

As shown in FIG. 4, at step 205, the method 200 can perform a second annotation on the feature parts of the individual cells in the obtained living cell images. The feature parts have been detailed in conjunction with FIG. 1 previously, and the description thereof is omitted here. In one embodiment, the living cell images obtained at step 205 may use the large sample of living cell images obtained at step 202, and the second annotation of feature parts may be based on the first annotation of the individual cells at step 202. With such a setup, it is possible to reduce the quantity and image processing times of living cell images while ensuring the number of training samples, thus lowering equipment wear and enhancing training speed. In another embodiment, the living cell images at step 205 can be obtained separately and distinct from the living cell images obtained at step 202. In yet another embodiment, the second annotation on the feature parts of the individual cells in the living cell images in the method 200 can be achieved by ways such as manual annotation or machine annotation. In one embodiment, in the method 200, the second annotation on the feature parts of the individual cells in the living cell images can be achieved by using an annotation model.

Next, the process moves to step 206, where the method 200 can use the second annotated living cell images to train a second deep neural network model to obtain the cell segmentation model. In one embodiment, the second deep neural network model may be constructed based on at least one of models such as U-net, FCN, DeepLab, E-net, etc. By training the second deep neural network model with the second annotated living cell images, the parameters and weights of the second deep neural network model can be continuously optimized. In the method 200, the second annotated living cell images are used to train the second deep neural network model to obtain the trained second deep neural network model, which can be referred to as the cell segmentation model.

According to another embodiment of the present disclosure, at step 206, during training of the second deep neural network model, the method 200 can further include applying image data enhancement processing to the living cell images. The image data enhancement processing can include at least one of spatial transformation processing, scaling resizing processing, and image brightness adjustment processing, etc.

It should be noted that in the method 200, step 205 or step 206 and step 204, etc. can be executed simultaneously or in any order. In another embodiment, when executing step 207, the method 200 can also simultaneously execute steps 205 and 206, continuously optimizing and updating the parameters of the cell segmentation model, thus enabling continuous adjustments and improvements to the accuracy of feature part segmentation.

According to an embodiment of the present disclosure, the output part of the cell segmentation model can adopt a single-branch multi-class segmentation structure or a multi-branch single-class segmentation structure. For ease of understanding, illustrative description will be provided in conjunction with FIGS. 5A and 5B.

Figure 5A:
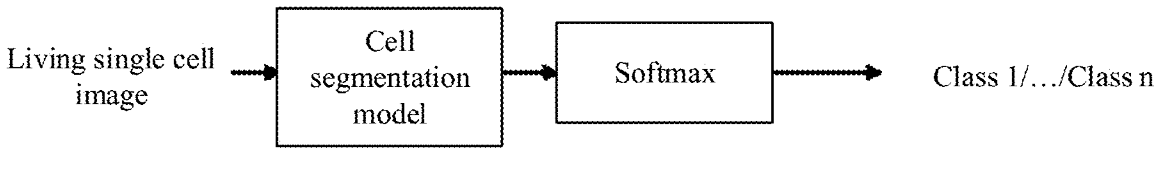
FIG. 5A is a schematic diagram showing a single-branch multi-class segmentation structure according to an embodiment of the present disclosure.

FIG. 5A shows a schematic diagram of a single-branch multi-class segmentation structure according to an embodiment of the present disclosure. As shown in FIG. 5A, a living single cell image is input into the cell segmentation model, and the softmax function is used for classification at the output, resulting in the segmentation results for multiple feature parts. In one embodiment, the living single cell can be a living single sperm, and Classes 1 to n shown in FIG. 5A may represent respectively information related to the head, the vacuole, the midpiece, and other feature parts of the living single sperm.

Figure 5B:
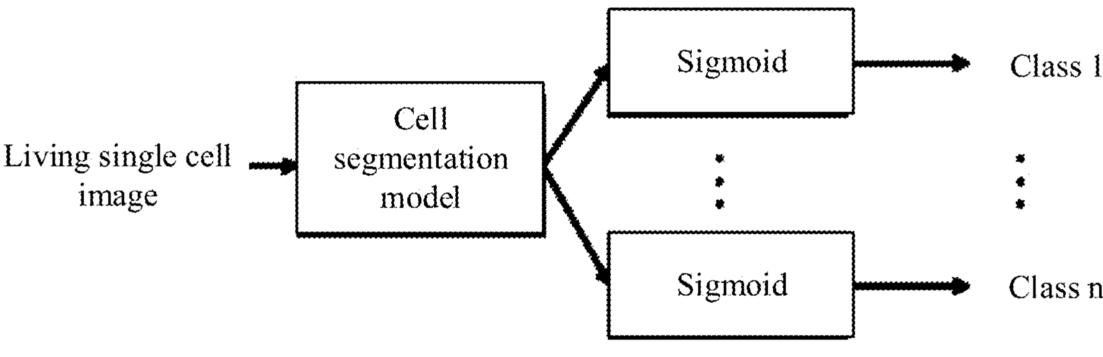
FIG. 5B is a schematic diagram showing a multi-branch single-class segmentation structure according to another embodiment of the present disclosure.

FIG. 5B shows a schematic diagram of a multi-branch single-class segmentation structure according to an embodiment of the present disclosure. As shown in FIG. 5B, a living single cell image can be input into the cell segmentation model, and multiple sigmoid functions can be used for classification at the output, resulting in the segmentation results for multiple feature parts. In one embodiment, the living single cell can be a living single sperm, and Classes 1 to n shown in FIG. 5B may represent respectively information related to the head, the vacuole, the midpiece, and other feature parts of the living single sperm. The output structures as shown in FIGS. 5A and 5B can be chosen as required.

Return back to FIG. 4. Through the following description, those skilled in the art will understand that steps 208, 209 and 210 of the method 200 may be a specific implementation of step 106 of the method 100 shown in FIG. 1, so the previous description of step 106 of the method 100 in FIG. 1 also applies to steps 208, 209 and 210 of the method 200.

As shown in FIG. 4, at step 208 of the method 200, morphological analysis may be performed on the segmented feature part(s) of the living single cell(s), so as to obtain geometric parameter(s) of the feature part(s). For example, in an embodiment, the geometric parameter can include at least one of length, width, area, ellipticity, quantity, position, etc. The geometric parameter(s) can be determined by the morphological characteristics of the feature parts. In another embodiment, a living single cell may be a living single sperm, and its feature parts may include, for example, the head and the vacuole of a single sperm. The method 200 performs morphological analysis on the head and the vacuole of a single sperm to obtain geometric parameters about the head, such as head length, head width, head area, and ellipticity, and geometric parameters about the vacuole, such as vacuole area, vacuole number and vacuole position, etc.

As further shown in FIG. 4, at step 209 of the method 200, sharpness of the living single cell images can be measured, in order to select a clear single cell image. In the method 200, sharpness measuring can be performed on the living single cell images as extracted at step 204, so as to screen out one or more single cell images with clear morphology. Sharpness measurement can effectively exclude living single cell images captured when the activity of living single cells is flipped or fluctuated up and down (i.e., out of focal plane). Due to the low definition of such images or the posture of living single cells in the images is not conducive to detection and analysis, excluding such images and screening out single cell images with clear morphology can not only reduce data amount to be processed in subsequent image analysis, but also effectively improve the accuracy of the final determined morphological parameters of living single cells.

According to one embodiment of the present disclosure, at step 209 of the method 200, measuring the sharpness of the living single cell image may include: evaluating the sharpness of the living single cell images with one or more focusing evaluation operators. The focusing evaluation operators can include, for example, at least one of image Gray Level VAriance (GLVA), image Gray Level Variance Normalized (GLVN), and Absolute Center MOment (ACMO). In order to facilitate understanding, the above focusing evaluation operators will be illustrated by example.

The image Gray Level VAriance (GLVA) mentioned above can be calculated as follow:

$$GLVA = \frac{1}{mn}\sum_{i=1}^{m}\sum_{j=1}^{n}\left(I_{i,j} - \bar{I}\right)^2$$

$$\bar{I} = \frac{1}{mn}\sum_{i=1}^{m}\sum_{j=1}^{n} I_{i,j}$$

Wherein, $\bar{I}$ represents the average value of the grayscale image I, the size of the image I is m×n, and $I_{i,j}$ represents the gray level of the pixel (i, j) in the image. The smaller the value of GLVA, the better the clarity of the image I.

The image Gray Level Variance Normalized (GLVN) mentioned above can be calculated as follow:

$$GLVN = \frac{1}{mn\bar{I}}\sum_{i=1}^{m}\sum_{j=1}^{n}\left(I_{i,j} - \bar{I}\right)^2$$

Wherein, $\bar{I}$ represents the average value of the grayscale image I, the size of the image I is m×n, and $I_{i,j}$ represents the gray level of the pixel (i, j) in the image. The smaller the value of GLVN, the better the clarity of the image I.

Furthermore, the Absolute Center MOment (ACMO) can be calculated as follow:

$$ACMO = \sum_{k=1}^{L}|k - \mu|P_k$$

Wherein, ACMO is a measure based on the grayscale histogram H, μ represents the average value of the grayscale histogram H, L represents the number of grayscale levels in the grayscale histogram H, $P_k$ represents the frequency of the k-th gray level. The smaller the value of ACMO, the better the clarity of the image.

Next, returning to FIG. 4 for further description, at step 210 of the method 200, the morphological parameter of the living single cell(s) can be determined based on the geometric parameter and the sharpness. In one embodiment, the method 200 can determine the morphological parameter of the living single cell(s) based on the geometric parameter of the feature part(s) of the single cell image with clear morphology as screened out at step 209. According to another embodiment of the present disclosure, at step 210, the method 200 may include: performing a first ranking of the living single cell images based on values of the geometric parameters; performing a second ranking of the living single cell images based on values of the sharpness; and based on the ranking, selecting one or more images that are in the forefront in both the first ranking and the second ranking, and using an average value of the geometric parameters of the selected one or more images as the morphological parameter of the living single cell(s). In yet another embodiment, the method 200 can determine the number of groups of the first ranking based on the types of geometric parameters. To facilitate understanding, a specific example will be described below.

In a specific embodiment, taking the living single cell as a living single sperm, for example, its feature part can include the head of the single sperm, and the geometric parameters of the head can be set as the head area, the head length, and the head width. The method 200 can, based on the size of the head area, the head length, and the head width, perform three groups of the first ranking of the living single cell images, which can include a first group of the first ranking based on the head area from large to small, a second group of the first ranking based on the head length from large to small, and a third group of the first ranking based on the head width from large to small. The method 200 can further perform a second ranking based on the sharpness of the living single cell images, such as according to the focusing evaluation operator value from small to large for the second ranking. Then, based on the three groups of the first ranking and one group of the second ranking (referred to as four groups of rankings), the method 200 can select one or more images that rank in the forefront in all of the four groups of rankings. For example, in one embodiment, the method 200 can select images that appear in the top ten in all four groups. Next, the method 200 can take the average value of the geometric parameters of the selected one or more images as the morphological parameter of the live single cell.

The deep neural network-based method 200 for living cell morphology detection according to an embodiment of the present disclosure has been described above in conjunction with FIG. 4. It should be understood by those skilled in the art that the above description is illustrative and not limiting. For example, step 209 is not limited to the order shown in the figure; it can also be adjusted to be performed before step 208, which may be beneficial to reduce the number of images to be processed during morphological analysis. Furthermore, the segmentation at step 207 is not limited to segmenting living single cell images. In one embodiment, the segmentation may also segment single cell images within the focal plane range. An exemplary description will be given below in conjunction with FIGS. 6 and 7.

Figure 6:
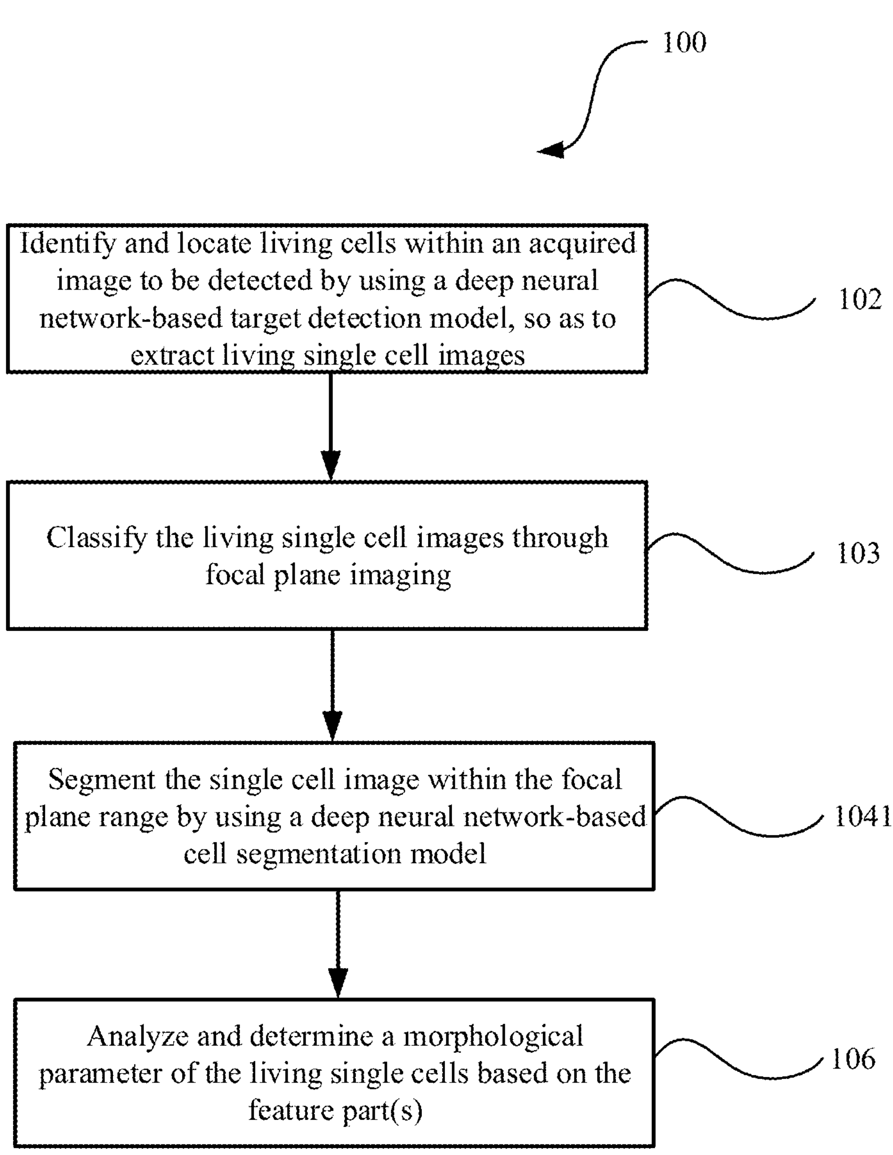
FIG. 6 is another flowchart showing a deep neural network-based method for living cell morphology detection according to an embodiment of the present disclosure.

FIG. 6 is another flowchart showing a deep neural network-based method for living cell morphology detection according to an embodiment of the present disclosure. Through the following description, it can be understood that the method shown in FIG. 6 is another specific embodiment of the method shown in FIG. 1. As shown in FIG. 6, at step 102, the method 100 may use a deep neural network-based target detection model to identify and locate one or more living cells within one or more acquired images to extract one or more living single cell images. Step 102 has been described in detail earlier in conjunction with FIG. 1, and is not repeated here.

Next, at step 103, the method 100 may include classifying the living single cell images through focal plane imaging to select a single cell image within the focal plane range. Since living cells may often deviate from the focal plane during activity, and out-of-focus images are unsuitable for morphology detection due to blurriness, at step 103, the method 100 can include classifying the living single cell images based on the degree of deviation from the focal plane during imaging of the living single cells, to screen out clear single cell images within the focal plane range. In one embodiment, the focal plane (or focus plane) may be, for example, the focal plane when the microscope captures the images to be detected.

The focal plane range described above may be a range of planes that can be clearly imaged and centered on the focal plane. For example, in another embodiment, the focal plane range may be a plane range from 1 micron above to 1 micron below the focal plane. According to another embodiment of the present disclosure, at step 103, the method 100 may include using a focal plane classification model to classify the living single cell images through focal plane imaging. According to the method 100 of the present disclosure, performing focal plane imaging classification on living single cell images before segmenting them with a cell segmentation model, can exclude most blurred living single cell images, thereby effectively reducing the image processing load and increasing processing speed. Compared to the implementation of excluding out-of-focus images through sharpness measurement, the approach of screening out single cell images within the focal plane range through focal plane imaging classification will be more accurate and intuitive.

Then, the process proceeds to step 1041, where the method 100 may include using a deep neural network-based cell segmentation model to segment the single cell images within the focal plane range to obtain one or more feature parts of the living single cells. Since the single cell images within the focal plane range are relatively clear, segmenting the single cell images within the focal plane range in the method 100 can not only reduce the image processing burden but also improve the accuracy and efficiency of the segmentation results. Through the above description, it can be understood that step 1041 may be a specific implementation of step 104 shown in FIG. 1, so the previous descriptions regarding step 104 and its embodiments can also apply to step 1041.

As further shown in FIG. 6, at step 106, the method 100 may include analyzing and determining one or more morphological parameters of the living single cell based on the feature part(s). This step has been described in detail earlier in conjunction with FIG. 1, and is not repeated here.

The deep neural network-based method for living cell morphology detection according to another embodiment of the present disclosure has been described above in conjunction with FIG. 6. Those skilled in the art can understand that the above description is illustrative and not limiting. For example, the focal plane range can be adjusted and selected as needed, for example based on factors such as the type, size, and imaging effects of living cells. In another embodiment, the method 100 may further implement steps such as focal plane imaging classification of living single cell images based on a deep neural network model, and exemplary descriptions will be given below in conjunction with FIG. 7.

Figure 7:
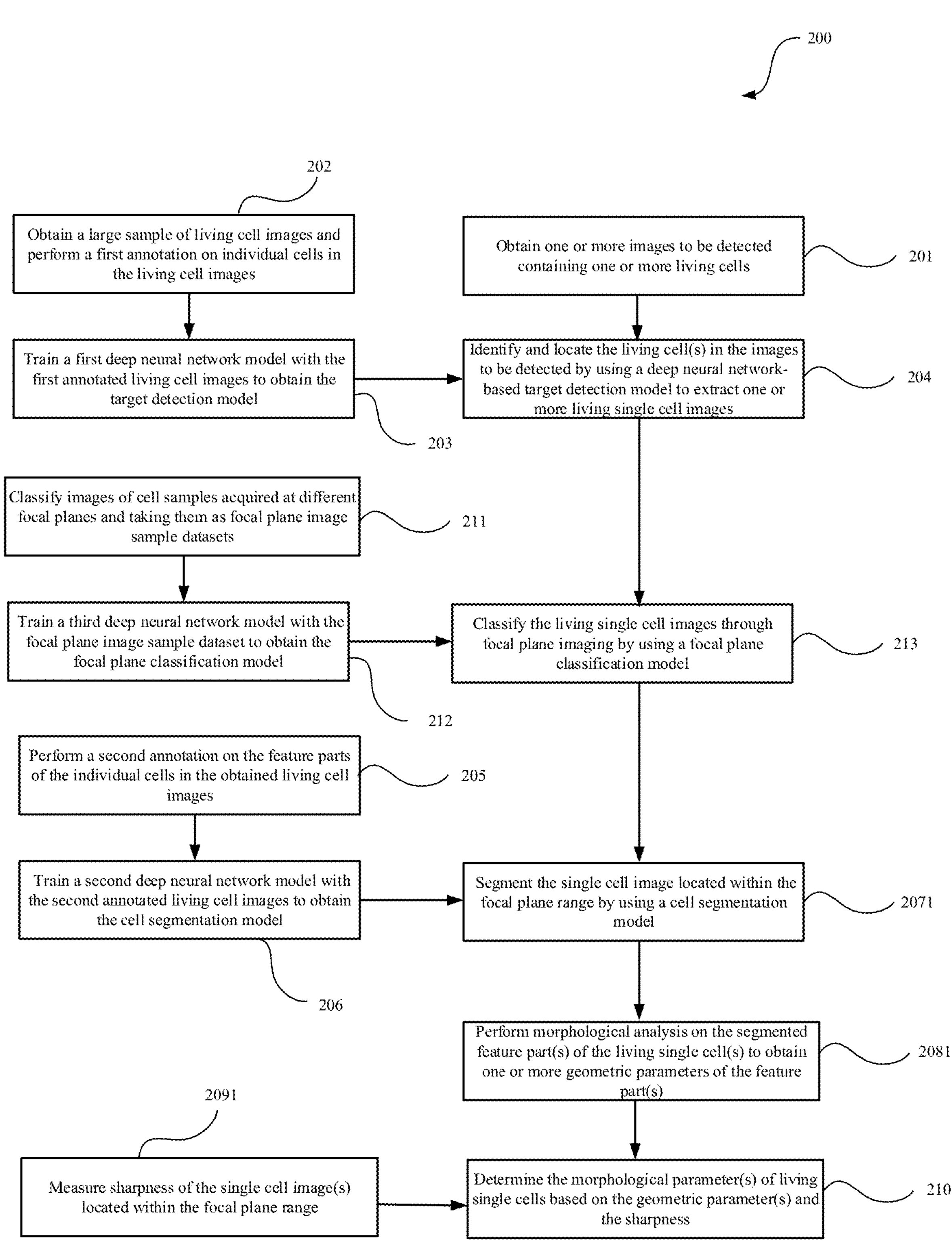
FIG. 7 is another detailed flowchart showing a deep neural network-based method for living cell morphology detection according to an embodiment of the present disclosure.

FIG. 7 is another detailed flowchart showing a deep neural network-based method for living cell morphology detection according to an embodiment of the present disclosure. Through the description below, those skilled in the art can understand that the method 200 shown in FIG. 7 can be a specific implementation of the method 100 shown in FIG. 6, and is also a preferred embodiment based on the method 200 shown in FIG. 4. Therefore, the description in conjunction with the method 100 shown in FIG. 6 and the method 200 shown in FIG. 4 is also applicable to the description below.

As shown in FIG. 7, steps 201, 202, 203, and 204 are the same or similar to those described in conjunction with FIG. 4, and are not further elaborated here. The method 200, after performing step 204, may proceed to step 213. At step 213, the method 200 may include using a focal plane classification model to classify the living single cell images through focal plane imaging, to screen out single cell images located within the focal plane range. In one embodiment, the focal plane classification model may use at least one of the classification models such as Resnet and Densenet. In another embodiment, in the method 200, before using the focal plane classification model, the focal plane classification model may be accelerated by using, for example, network structure acceleration, model inference acceleration, and/or model pruning acceleration. Network structure acceleration, model inference acceleration, and model pruning acceleration have already been described in detail in conjunction with FIG. 1 and are not further described here. Further, to improve the accuracy of focal plane imaging classification, the present embodiment also provides a preferred way to build the focal plane classification model, as further shown in FIG. 7, including steps 211 and 212, which will be described in detail below.

At step 211, the method 200 can include classifying images of cell samples acquired at different focal planes and taking them as focal plane image sample datasets. The cell samples mentioned here may include cells in relatively fixed positions. For example, in one embodiment, the cell samples may include frozen cells, where the cells can be kept in a fixed position without losing activity through freezing. The method 200 may include acquiring images at different focal planes by moving the cell samples to different focal positions, and classifying and annotating the sample images based on the physical position of the focal plane at the time of image acquisition. The focal plane image sample dataset may include one or more sample images and their classification annotation and other information.

Next, at step 212, the method 200 can include using the focal plane image sample dataset to train a third deep neural network model to obtain the focal plane classification model. In one embodiment, the third deep neural network model may be constructed based on at least one model such as Resnet, Densenet, etc. By training the third deep neural network model using the focal plane image sample dataset, the parameters and weights of the third deep neural network model can be continuously optimized. The method 200 uses the focal plane image sample dataset to train the third deep neural network model to obtain the trained third deep neural network model, and the trained third deep neural network model can be referred to as the focal plane classification model.

According to an embodiment of the present disclosure, at step 212, the method 200 may further include applying image data enhancement processing to the focal plane image sample dataset during training the third deep neural network model, where the image data enhancement processing may include at least one of spatial transformation processing, scaling resizing processing, and image brightness adjustment processing.

It should be noted that in the method 200, step 211 or step 212 may not necessarily follow step 204 in sequence and may be carried out simultaneously. In another embodiment, when the method 200 executes step 213, it may also simultaneously execute step 211 and step 212 to continuously optimize parameters of the focal plane classification model, thus enabling continuously adjustments and improvements in the accuracy of focal plane classification.

Further, after step 213, the method 200 may proceed to step 2071. At step 2071, the method 200 may include using a cell segmentation model to segment the single cell image located within the focal plane range, to obtain one or more feature parts of the living single cell within the focal plane range. It can be understood that at step 2071 of the method 200, only those single cell images within the focal plane range need to be performed segmentation of feature parts, reducing image data amount to be processed and enhancing segmentation efficiency and accuracy. In one embodiment, the cell segmentation model at step 2071 can be obtained through steps 205 and 206 performed by the method 200, where steps 205 and 206 have been detailed earlier with reference to FIG. 4, so they will not be further described here.

Then, the process may move on to step 2081, where the method 200 may include performing morphological analysis on the segmented feature part(s) of the living single cell(s) located within the focal plane range, to obtain one or more geometric parameters of the feature part(s). Method for morphological analysis can refer to the previous description about step 208 in FIG. 4.

As further shown in FIG. 7, at step 2091, the method 200 may include measuring sharpness of the single cell image(s) located within the focal plane range, to further screen out clear single cell image(s). The method 200 may include measuring the sharpness of the single cell image(s) within the focal plane ranges selected at step 213, to select one or more single cell images with clear morphology. In some scenarios, sharpness measurement here may be understood as an approach to screen out front-facing images of living single cells, excluding images of living single cells acquired when they are flipping (such as side images). Since the posture of living single cells affects detection and analysis, excluding images with poor posture can not only further reduce data amount in subsequent image analysis but also effectively enhance the accuracy of the final determined morphological parameters of living single cells. According to one embodiment of the present disclosure, the sharpness measurement of single cell images within the focal plane range at step 2091 may include: using one or more focusing evaluation operators to assess the sharpness of the single cell images.

Furthermore, at step 210, the method 200 may include determining the morphological parameter(s) of living single cells based on the geometric parameter(s) obtained at step 2081 and the sharpness obtained at step 2091. The way to determine the morphological parameter(s) can refer to the related description of step 210 in FIG. 4, so it will not be further described here.

Through the above description of the technical solution of the method for living cell morphology detection of the present disclosure and multiple embodiments thereof, it can be understood by those skilled in the art that according to the method of the present disclosure, a non-destructive and precise detection of living cell morphology can be achieved by performing operations such as identifying, locating, and feature part segmenting on the living cell within images to be detected, thus reducing the subjective errors of manual detection, and assisting in or partially replacing the clinical diagnosis and assessment work by doctors. Taking sperm morphology detection as an example, compared with existing technology based on dead sperm morphology detection, the method of the present disclosure can maintain the physiological function and DNA genetic material integrity of the sperm, and does not need to make staining slides, etc., thus eliminating the influence of interference factors such as slide staining dehydration on detection results, and having advantages such as high accuracy, high stability, simple process, short time, etc. Most importantly, the living sperm screened by the method of the present disclosure can be used clinically (such as IVF, etc.). In the above embodiments of the present disclosure, implementations such as focal plane imaging classification, sharpness measurement, etc., are also provided, which can accurately screen out images that are clear, pose-suitable, and morphologically clear, in order to further improve the accuracy and reliability of detection results, and reduce image processing burden thereby increasing the detection rate, etc.

Furthermore, in the above description, the present disclosure further provides embodiments based on deep learning such as the target detection model, the cell segmentation model, and the focal plane classification model, the principle of its feature hierarchical abstraction and autonomous learning is closer to the human brain working mode, thus it can extract feature information that traditional methods cannot capture, thereby improving the accuracy of living cell morphology detection. In some embodiments, the target detection model, the cell segmentation model, etc., obtained by training with large samples of living cell images can significantly enhance the generalization ability and robustness of living cell identification, location, and segmentation, and can greatly reduce the influence of interference factors such as shooting environment, brightness, impurities on morphological analysis, and has good adaptability and expandability. Through training and continuous iterative updates, the target detection model, the cell segmentation model, and the focal plane classification model of the present disclosure can meet the needs of living cell morphology analysis under different feature part detection (such as sperm head, midpiece, or tail, etc.), different focal plane classification methods, different imaging methods (such as differential interference contrast, bright field, dark field, phase contrast, etc.), and different magnification conditions of living cells.

In a second aspect of the present disclosure, a device for living cell morphology detection based on deep neural networks is provided, which may include a positioning module, which may be configured to identify and locate a living single cell within an acquired image to be detected by using a deep neural network-based target detection model, to extract a living single cell image; a segmentation module, which may be configured to segment the living single cell image by using a deep neural network-based cell segmentation model, to obtain a feature part of the living single cell; and a morphology analysis module, which may be configured to analyze and determine a morphology parameter of the living single cell based on the feature part.

According to an embodiment of the present disclosure, the device for living cell morphology detection of the present disclosure may further include: a focal plane classification module, which may be configured to perform focal plane imaging-based classification on the living single cell image, to select a single cell image located within the focal plane range; and the segmentation module may further be configured to segment the single cell image located within the focal plane range.

In a third aspect of the present disclosure, an apparatus for living cell morphology detection based on deep neural networks is provided, which may include, at least one processor; a memory, which can store program instructions, when the program instructions are executed by the at least one processor, enabling the apparatus to perform any one of the methods described in the first aspect of this disclosure. An illustrative description will be given in conjunction with FIG. 8.

Figure 8:
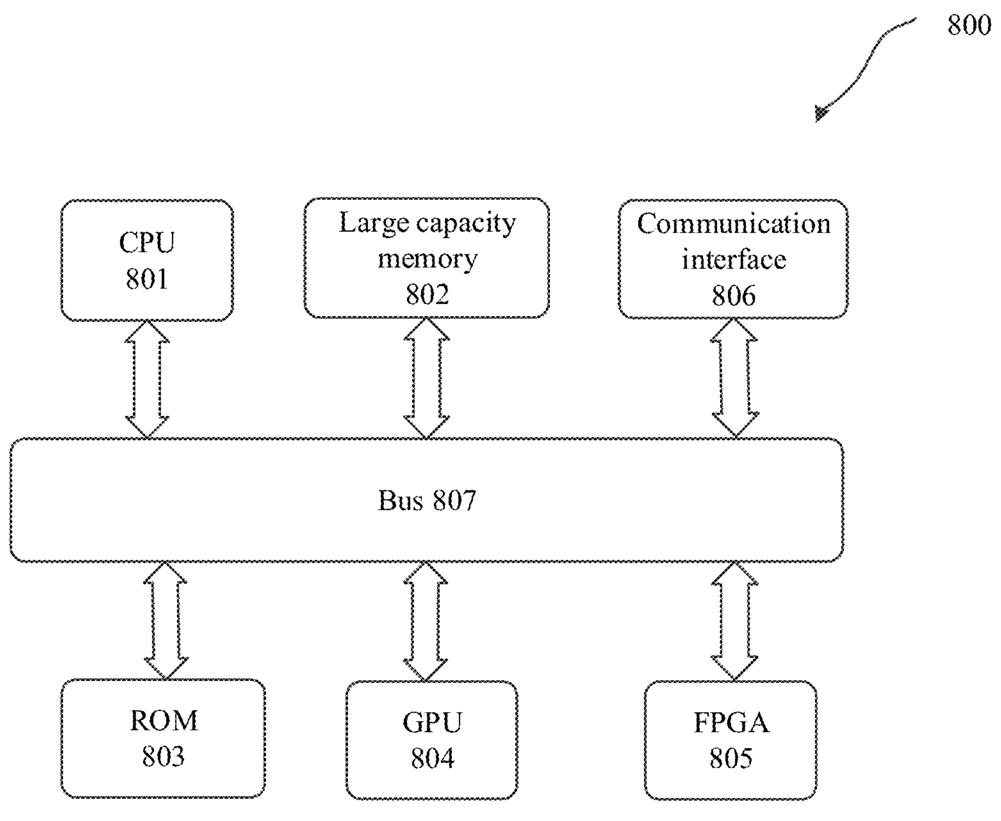
FIG. 8 is a schematic diagram showing an apparatus for living cell morphology detection based on deep neural networks according to an embodiment of the present disclosure.

FIG. 8 is a schematic diagram showing an apparatus for living cell morphology detection based on deep neural networks according to an embodiment of the present disclosure. The apparatus 800 can be used to identify and locate a living cell within an image to be detected, segment feature part(s), and determine morphological parameters, etc., in order to implement the living cell morphology detection solution of the present disclosure described in conjunction with FIGS. 1-7.

As shown in FIG. 8, the apparatus 800 may include a CPU 801, which may be a general purpose CPU, dedicated CPU, or other information processing and program execution unit. Furthermore, the apparatus 800 can further include a large capacity memory 802 and a read-only memory (ROM) 803, wherein the large capacity memory 802 may be configured to store various data, including various program as required by the target detection model, the cell segmentation model, etc., and the ROM 803 can be configured to store data required for initializing the various functional modules of the living cell morphology detection of the apparatus 800, basic input/output drivers, and booting the operating system.

Additionally, the apparatus 800 may include other hardware or components, such as the illustrated Graphics Processor Unit ("GPU") 804 and Field Programmable Gate Array ("FPGA") 805, etc. It is understood that although various hardware or components are shown in the apparatus 800, this is merely illustrative and not limiting, and those skilled in the art may add or remove corresponding hardware as needed.

The apparatus 800 of the present disclosure may further include a communication interface 806, allowing it to connect to a Local Area Network/Wireless Local Area Network (LAN/WLAN), and subsequently to, for example, a control terminal or the Internet ("Internet"). Alternatively or additionally, the apparatus 800 of the present disclosure may connect directly to the Internet or cellular network through the communication interface 806 via wireless communication technology, such as the third generation ("3G"), fourth generation ("4G"), or fifth generation ("5G") wireless communication technology. In some application scenarios, the apparatus 800 of the present disclosure may access external network servers and possible databases as needed to obtain various known information, data, and modules, and can remotely store various detected data.

The above-mentioned CPU 801, large-capacity memory 802, Read Only Memory ("ROM") 803, GPU 804, FPGA 805, and communication interface 806 of the apparatus 800 of the present disclosure may be interconnected via a bus 807, and data exchange with peripheral devices can be implemented through the bus. In one embodiment, through the bus 807, the CPU 801 may control other hardware components and peripheral devices in the apparatus 800.

In operation, the CPU 801 or GPU 804 of the apparatus 800 of the present disclosure may receive data via the bus 807 and call computer program instructions or code stored in the memory 802 (e.g., code related to living cell morphology detection based on deep neural networks), to detect received images to be detected. Specifically, the CPU 801 or GPU 804 may execute a deep neural network-based target detection model to identify and locate living cell(s) within the images to be detected, to obtain live single cell image(s), etc. Simultaneously, the CPU 801 or GPU 804 of the apparatus 800 may also execute a cell segmentation model to segment the feature part(s) of the living single cell image(s). Then, the CPU 801 or GPU 804 can analyze and determine the morphological parameter(s) of the living single cell(s) based on the feature part(s). After the CPU 801 or GPU 804 has determined the morphological parameter(s) of the living single cell(s) by executing the detection program, the results can be uploaded through, for example, the communication interface 806, to the network, such as a remote database or an external control terminal.

It should also be understood that any module, unit, component, server, computer, terminal, or apparatus for executing instructions in the embodiments of the present disclosure may include or otherwise access computer-readable media, such as storage media, computer storage media, or data storage devices (removable and/or non-removable) such as disks, optical discs, or tapes. Computer storage media may include volatile and non-volatile, removable and non-removable media implemented in any method or technology for storage of information such as computer-readable instructions, data structures, program modules, or other data.

In a fourth aspect of the present disclosure, a computer-readable storage medium is provided, capable of storing a program for living cell morphology detection based on deep neural networks. When the program is run by a processor, it carries out the method described in any item of the first aspect of the present disclosure.

The computer-readable storage medium can be any appropriate magnetic storage medium or magneto-optical storage medium, such as Resistive Random Access Memory (RRAM), Dynamic Random Access Memory (DRAM), Static Random-Access Memory (SRAM), Enhanced Dynamic Random Access Memory (EDRAM), High-Bandwidth Memory (HBM), Hybrid Memory Cube (HMC), etc., or any other medium that can be used to store the required information and can be accessed by an application, module, or both. Any such computer storage medium can be part of an apparatus or accessible or connectable to the apparatus. Any application or module described in the present disclosure can be implemented using computer-readable/executable instructions that can be stored or otherwise retained by such computer-readable media.

Figure 9:
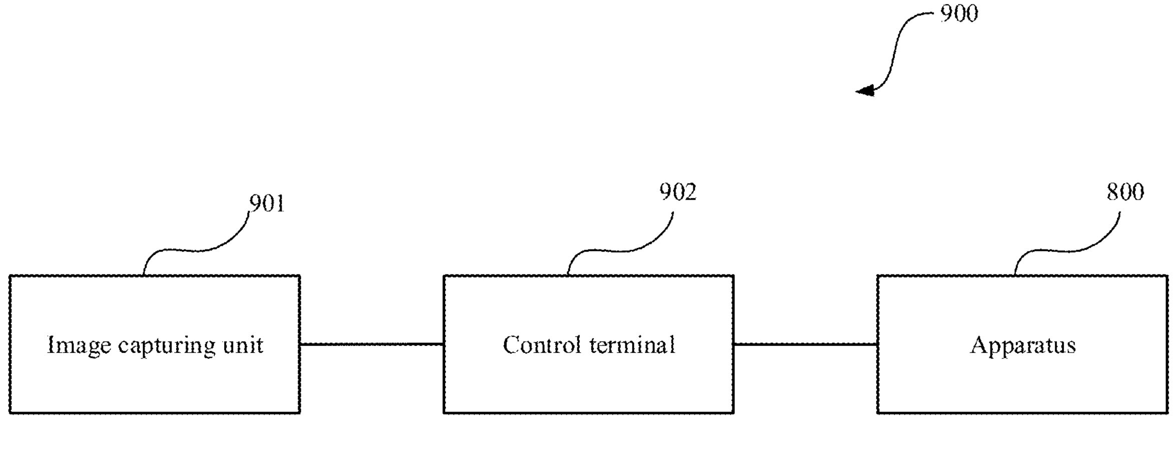
FIG. 9 is a schematic diagram showing a system for living cell morphology detection based on deep neural networks according to an embodiment of the present disclosure.

In a fifth aspect of the present disclosure, a system 900 for living cell morphology detection based on deep neural networks is provided, as shown in FIG. 9, and may include: an image capturing unit 901, which can be used to capture an image containing a living cell to be detected; a control terminal 902, which can be communicatively connected to the image capturing unit 901 and used to receive the image to be detected sent from the image capturing unit 901; and an apparatus 800 as described in the third aspect of the present disclosure, which can be communicatively connected to the control terminal 902, used to receive the image to be detected sent from the control terminal 902, perform detection on the image, and send detection results to the control terminal 902.

According to an embodiment of the present disclosure, the image capturing unit 901 may include at least one of optical microscopic imaging devices (such as microscopes), cameras, light source devices, etc. The control terminal 902 can be connected to the image capturing unit 901 via wired or wireless means. In another embodiment, the control terminal 902 may include one or more of desktops, laptops, tablets, smartphones, etc. The apparatus 800 can be connected to the control terminal 902 via wired or wireless means to enable information exchange. The apparatus 800 can send control information to obtain the images to be detected and send the detection results to the control terminal 902. The control terminal 902 can send the images to be detected, status information, etc., to the apparatus 800 in real time. According to an embodiment of the present disclosure, the apparatus 800 may include an inference engine. In a specific embodiment, before using the target detection model, the cell segmentation model, or the focal plane classification model, acceleration such as network structure acceleration, model inference acceleration, and/or model pruning acceleration can be applied to one or more of the target detection model, the focal plane classification models, and the cell segmentation models, etc., and then run on the inference engine to detect the received images, facilitating improved inference speed of the target detection model, the cell segmentation models, or the focal plane classification model, and detection speed of the images to be detected.

In some application scenarios, the image capturing unit 901, the control terminal 902, and the apparatus 800 can be deployed through an internal network, such as being connected to a same intranet through routers or switches, etc. With this arrangement, it is possible to avoid public access to the system of the disclosure, thereby better ensuring the information security within the system. Especially in the case of medical images or other information involving personal privacy, the system of the disclosure has good deployment value and application prospects. Furthermore, in some embodiments, the apparatus 800 can connect to remote servers to accept remote updates and other operations. This arrangement can better achieve system updates and maintenance, and reduce the time and cost of on-site maintenance. In other embodiments, the apparatus 800 may continuously iterate and update model parameters through local self-learning, thus serving the local connected control terminal better, and better adapting to locally acquired image data and detection environments, etc., to ensure the accuracy and reliability of detection.

In a specific embodiment, during the information interaction between the apparatus 800 and the control terminal 902, the network data packet format can be defined as 32 bits data size+16 bits data ID+data. The 32 bits data size ensures that the program is aware of the data's start and reception range, while the 16 bits data ID ensures that the program handles different data types differently. The data part can be decoded according to the data type. The system of the disclosure can implement real-time requirements through multi-process multi-queue, and an exemplary description will be given below.

Specifically, the apparatus 800 can use five process queues to save data at different stages, including: a first stage, a network process receives network data stream in real-time, saves it into a buffer queue process queue; a second stage, a buffer worker process processes the received buffer queue data in real-time, parsing it into network message packets, and passing it into a msg_queue process queue; a third stage, a msg_worker process processes the msg_queue data in real-time, extracting control commands and image data, and passing the image data into a img_queue process queue; a fourth stage, a batch worker process processes the img_queue data in real-time, combining batch size images into one data and passing it into a batch_queue process queue; and a fifth stage, a tensor worker process processes the batch_queue data in real-time, performing preprocessing to convert it into tensor data that apparatus 800 can use, then performing inference to get the final result. Detection result of the apparatus 800 can be transmitted back to the control terminal for result display.

Although embodiments of the disclosure are as above, the content described is only embodiments adopted for ease of understanding the disclosure and is not intended to limit the scope and application scenarios of the disclosure. Any technical personnel in the technical field to which the disclosure pertains may make any modifications and changes in form and detail without departing from the spirit and scope disclosed by the disclosure. However, the patent protection scope of the disclosure must still be defined by the scope delineated in the appended claims.

What is claimed is:

1. A deep neural network-based method for detecting living cell morphology, the method comprising:

identifying and locating one or more living cells within an acquired image to be detected by using a deep neural network-based target detection model, so as to extract one or more living single cell images;

classifying living single cell images through focal plane imaging to select a single cell image located within the focal plane range;

segmenting the single cell image located within the focal plane range by using a deep neural network-based cell segmentation model, so as to obtain one or more feature parts of the one or more living single cells; and analyzing and determining a morphological parameter of the one or more living single cells based on the one or more feature parts-;

wherein the classifying of the living single cell images includes:

classifying images of cell samples acquired at different focal planes and taking them as focal plane image sample datasets;

training a third deep neural network model using the focal plane image sample datasets to obtain a focal plane classification model; and using the focal plane classification model to classify living single cell images through focal plane imaging to select a single cell image within the focal plane range.

2. The method of claim 1, further comprising:

prior to using the deep neural network-based target detection model, obtaining samples of living cell images;

performing a first annotation on individual cells in the living cell images; and training a first deep neural network model using the first annotated living cell images to obtain the target detection model.

3. The method of claim 2, wherein the training of the first deep neural network model further comprises:

during the training of the first deep neural network model, applying image data enhancement processing to the living cell images, where the image data enhancement processing includes at least one of spatial transformation processing, scale resizing processing, and image brightness adjustment processing.

4. The method of claim 1, further comprising:

prior to using the deep neural network-based cell segmentation model, performing a second annotation on feature parts of individual cells in obtained living cell images; and training a second deep neural network model using the second annotated living cell images to obtain the deep neural network-based cell segmentation model.

5. The method of claim 4, wherein the training of the second deep neural network model further comprises:

during the training of the second deep neural network model, applying image data enhancement processing to the living cell images, where the image data enhancement processing includes at least one of spatial transformation processing, scale resizing processing, and image brightness adjustment processing.

6. The method of claim 1, wherein an output part of the deep neural network-based cell segmentation model adopts a single-branch multi-class segmentation structure or a multi-branch single-class segmentation structure.

7. The method of claim 1, wherein the living cell includes a living sperm, and the feature part includes at least one of a sperm head, a vacuole, a midpiece, and a tail.

8. The method of claim 1, wherein the training of the third deep neural network model further comprises:

during the training of the third deep neural network model, applying image data enhancement processing to the focal plane image sample datasets, where the image data enhancement processing includes at least one of spatial transformation processing, scale resizing processing, and image brightness adjustment processing.

9. The method of claim 1, further comprising:

before using the target detection model, the deep neural network-based cell segmentation model, or the focal plane classification model, accelerating at least one of the target detection model, the deep neural network-based cell segmentation model, or the focal plane classification model through network structure acceleration, model inference acceleration, and/or model pruning acceleration.

10. The method of claim 1, wherein analyzing and determining the morphological parameter of the one or more living single cells includes:

performing morphological analysis on the segmented feature parts of the living single cell to obtain a geometric parameter of the feature parts;

measuring sharpness of the living single cell images to further select a clear single cell image; and determining the morphological parameter of the living single cell based on the geometric parameter and the sharpness.

11. The method of claim 10, wherein the measuring of the sharpness of the living single cell images includes:

evaluating the sharpness of the living single cell images with one or more focusing evaluation operators.

12. The method of claim 10, wherein the determining of the morphological parameter includes:

performing a first ranking of the living single cell images based on values of the geometric parameters;

performing a second ranking of the living single cell images based on values of the sharpness; and based on the ranking, selecting one or more images that are in the forefront in both the first ranking and the second ranking, and using an average value of the geometric parameters of the selected one or more images as the morphological parameter of the living single cell.

13. The method of claim 10, wherein the geometric parameter includes at least one of length, width, area, ellipticity, quantity, and position.

14. The method of claim 1, wherein the image to be detected includes at least one of a differential interference contrast image, a phase contrast image, a bright field image, and a dark field image.

15. A non-transient computer-readable storage medium storing a program for living cell morphology detection, which when run by a processor, carries out a deep neural network-based method for detecting living cell morphology, including:

identifying and locating one or more living cells within an acquired image to be detected by using a deep neural network-based target detection model, so as to extract one or more living single cell images;

classifying living single cell images through focal plane imaging to select a single cell image located within the focal plane range;

segmenting the single cell image located within the focal plane range by using a deep neural network-based cell segmentation model, so as to obtain one or more feature parts of the living single cell; and analyzing and determining a morphological parameter of the living single cell based on the one or more feature parts;

wherein the classifying of the living single cell images includes:

classifying images of cell samples acquired at different focal planes and taking them as focal plane image sample datasets;

training a third deep neural network model using the focal plane image sample datasets to obtain a focal plane classification model; and using the focal plane classification model to classify living single cell images through focal plane imaging to select a single cell image within the focal plane range.

16. A system for living cell morphology detection based on deep neural networks, the system comprising:

an image capturing unit for capturing an image containing a living cell to be detected, wherein the image capturing unit includes at least one of optical microscopic imaging devices, cameras, light source devices;

a control terminal communicatively connected to the image capturing unit and used to receive the image to be detected sent from the image capturing unit; and an apparatus for living cell morphology detection based on deep neural networks, communicatively connected to the control terminal, for receiving the image to be detected sent from the control terminal for detection, and sending detection results to the control terminal, wherein the apparatus comprising:

at least one processor;

a memory storing program instructions that, when executed by the at least one processor, enable the apparatus to perform a deep neural network-based method for detecting living cell morphology, including:

identifying and locating one or more living cells within an acquired image to be detected by using a deep neural network-based target detection model, so as to extract one or more living single cell images;

classifying living single cell images through focal plane imaging to select a single cell image located within the focal plane range;

segmenting the single cell image located within the focal plane range by using a deep neural network-based cell segmentation model, so as to obtain one or more feature parts of the living single cell; and analyzing and determining a morphological parameter of the living single cell(s) based on the one or more feature parts;

wherein the classifying of the living single cell images includes:

classifying images of cell samples acquired at different focal planes and taking them as focal plane image sample datasets:

training a third deep neural network model using the focal plane image sample datasets to obtain a focal plane classification model; and using the focal plane classification model to classify living single cell images through focal plane imaging to select a single cell image within the focal plane range.

17. The system of claim 16, wherein the apparatus includes an inference machine.

* * * * *